(12) United States Patent
Chen et al.

(10) Patent No.: US 9,969,701 B2
(45) Date of Patent: May 15, 2018

(54) SALTS AND CO-CRYSTALS OF LESINURAD

(71) Applicants: CRYSTAL PHARMATECH, INC., North Brunswick, NJ (US); CRYSTAL PHARMATECH CO., LTD., Jiangsu (CN); SUZHOU PENGXU PHARMATECH CO., LTD., Suzhou Jiangsu (CN)

(72) Inventors: Minhua Chen, Scotch Plains, NJ (US); Yanfeng Zhang, Suzhou (CN); Chaohui Yang, Suzhou (CN); Xiaoyu Zhang, Suzhou (CN); Peng Wang, Forest Hills, NY (US); Pixu Li, Suzhou (CN)

(73) Assignees: Crystal Pharmatech Co., Ltd., Suzhou, Jiangsu (CN); Suzhou Pengxu Pharmatech Co., Ltd., Suzhou, Jiangsu (CN)

( * ) Notice: Subject to any disclaimer, the term of this patent is extended or adjusted under 35 U.S.C. 154(b) by 0 days. days.

(21) Appl. No.: 15/106,361

(22) PCT Filed: Dec. 19, 2014

(86) PCT No.: PCT/US2014/071501
§ 371 (c)(1),
(2) Date: Jun. 20, 2016

(87) PCT Pub. No.: WO2015/095703
PCT Pub. Date: Jun. 25, 2015

(65) Prior Publication Data
US 2016/0347722 A1    Dec. 1, 2016

(30) Foreign Application Priority Data

Dec. 20, 2013 (CN) .......................... 2013 1 0706091
Dec. 23, 2013 (CN) .......................... 2013 1 0713789
(Continued)

(51) Int. Cl.
*C07D 249/12*    (2006.01)
*C07C 59/06*     (2006.01)
*C07D 207/16*    (2006.01)

(52) U.S. Cl.
CPC ............ *C07D 249/12* (2013.01); *C07C 59/06* (2013.01); *C07D 207/16* (2013.01); *C07B 2200/13* (2013.01)

(58) Field of Classification Search
None
See application file for complete search history.

(56) References Cited

U.S. PATENT DOCUMENTS

2009/0143316 A1    6/2009    Imamura et al.
2011/0268801 A1*  11/2011    Quart .................. C07D 249/12
                                                        424/474

FOREIGN PATENT DOCUMENTS

WO    2011/085009 A2    7/2011
WO    2011/159732 A1   12/2011
WO    2012/092395 A2    7/2012

OTHER PUBLICATIONS

Yicheng Wang et al., Recent Research Advances of Pharmaceutical Cocrystals, Progress in Pharmaceutical Sciences, 2013, vol. 37, No. 3, p. 120.

(Continued)

*Primary Examiner* — Timothy P Thomas
(74) *Attorney, Agent, or Firm* — VLP Law Group LLP

(57) ABSTRACT

Novel salts and cocrystals of lesinurad, processes for their preparation, pharmaceutical compositions comprising these new salt forms and co-crystals, and use of them for treating or delaying progression or onset of diseases or disorders related to activity of uric acid transport 1 (URAT1) proteins are disclosed. These novel forms were characterized by X-ray powder diffraction, differential scanning calorimetry, and other techniques. They can be readily prepared and are (Continued)

suitable for preparation of solid dosage forms owing to their ease of handling and superior pharmacological properties.

5 Claims, 14 Drawing Sheets

(30) Foreign Application Priority Data

Dec. 17, 2014 (CN) .......................... 2014 1 0783346
Dec. 17, 2014 (CN) .......................... 2014 1 0783347

(56) References Cited

OTHER PUBLICATIONS

Sao Yuan et al., Pharmaceutical Cocrystals, Progress in Chemistry, May 2010, vol. 22, No. 5, p. 829.

* cited by examiner

SALTS AND CO-CRYSTALS OF LESINURAD

CROSS REFERENCE TO RELATED APPLICATIONS

This application a U.S. national phase application of PCT/US2014/071501, filed Dec. 19, 2014, and claims priority to Chinese Patent Application No. 201310706091.6, filed on Dec. 20, 2013; Application No. 201310713789.0, filed on Dec. 23, 2013; Application No. 201410783347.8, filed on Dec. 17, 2014, and Application No. 201410783346.3, filed on Dec. 17, 2014, all of which are herein incorporated by reference in their entireties.

FIELD OF THE INVENTION

This invention relates to novel salts and co-crystals of lesinurad and their pharmaceutical compositions, methods of preparation, and methods of uses.

BACKGROUND OF THE INVENTION

Hyperuricemia is characterized by higher than normal blood levels of uric acid, sustained over long periods of time, often due to enhanced uric acid production (e.g., 10-20%) and/or reduced renal excretion (e.g., 80-90%) of uric acid. Hyperuricemia may be caused by numerous factors, such as obesity/weight gain, excessive alcohol use, excessive dietary purine intake, and certain medications, including low-dose aspirin, diuretics, niacin, cyclosporine, some high blood pressure drugs, some cancer chemotherapeutics, immunosuppressive and cytotoxic agents, and so on. In certain instances, hyperuricemia may be asymptomatic, but it may be associated with the following conditions: gout, gouty arthritis, uric acid stones in the urinary tract (urolithiasis), deposits of uric acid in the soft tissue (tophi), deposits of uric acid in the kidneys (uric acid nephropathy), and impaired kidney function, possibly leading to chronic and acute renal failure. Defective uric acid processing may lead to elevated levels of uric acid in the blood causing recurring attacks of joint inflammation (arthritis), uric acid deposits in and around the joints, tophaceous gout, the formation of tophi, decreased kidney function, and kidney stones. Approximately 3-5 million people in the United States suffer from attacks of gout. In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Lesinurad inhibits the uric acid transporter 1 (URAT1) protein, increasing uric acid excretion and thereby lowering serum uric acid (sUA), and is an investigational agent now in phase III clinical trial for treatment of gout. In top-line results from a Phase III study on gout patients who did not get benefit from treatment with allopurinol and febuxostat, lesinurad alone significantly reduced serum levels of uric acid.

Lesinurad is known by its chemical name as 2-((5-bromo-4-(4-cyclopropylnaphthalen-1-yl)-4H-1,2,4-triazol-3-yl)thio)acetic acid, having the structure of Formula I:

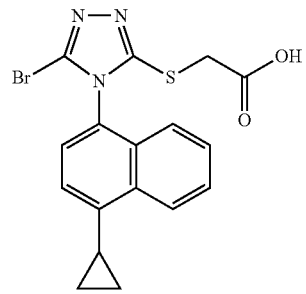

(I)

Two crystalline forms of lesinurad have been reported. (WO2012092395) In addition, polymorphic, crystalline and mesophase forms of lesinurad sodium salt have also been reported. (WO2011085009A2) However, due to unpredictable properties of different salts and their crystalline forms, novel salts or co-crystals of lesinurad and convenient methods to prepare them remain a great need.

SUMMARY OF THE INVENTION

The present invention provides new co-crystals and salts of lesinurad formed with various acids and bases. These co-crystals and salts of lesinurad can be prepared in environmentally friendly solvent systems in simple procedures as disclosed herein.

In one aspect, the present invention provides lesinurad salts selected from calcium salt, potassium salt, hydrochloride, ethanesulfonate (esylate), methanesulfonate (mesylate), 1,2-ethanedisulfonate, 2-hydroxyethanesulfonate (isethionate), and arginine salts.

In another aspect, the present invention provides crystalline forms of lesinurad salts, designated as calcium salt Form A, potassium salt Form A, hydrochloride Form A, hydrochloride Form B, esylate Form A, mesylate Form A, mesylate Form B, 1,2-ethanedisulfonate Form A, 1,2-ethanedisulfonate Form B, isethionate Form A, arginine salt Form A, respectively.

In another aspect, the present invention provides processes for preparation of lesinurad calcium salt Form A, potassium salt Form A, hydrochloride Form A, hydrochloride Form B, esylate Form A, mesylate Form A, mesylate Form B, 1,2-ethanedisulfonate Form A, 1,2-ethanedisulfonate Form B, isethionate Form A, arginine salt Form A, respectively.

In another aspect, the present invention provides a co-crystal composing lesinurad and a co-crystal former. The co-crystal former is selected from proline and glycolic acid.

In another aspect, the present invention provides processes for preparation of co-crystal composing lesinurad and a co-crystal former. The co-crystal former is selected from proline and glycolic acid.

In another aspect, the present invention provides solid pharmaceutical compositions comprising any of crystalline forms of lesinurad salts selected from calcium salt, potassium salt, hydrochloride, esylate, mesylate, 1,2-ethanedisulfonate, isethionate, arginine salt and co-crystal composing lesinurad and a co-crystal former selected from proline and glycolic acid, or any of combinations thereof.

In another aspect, the present invention provides methods of using any of crystalline forms of lesinurad salts selected from calcium salt, potassium salt, hydrochloride, esylate, mesylate, 1,2-ethanedisulfonate, isethionate, arginine salt and co-crystal composing lesinurad and a co-crystal former selected from proline and glycolic acid, or any of combinations thereof, in the manufacture of a medicament for treating or delaying the progression or onset of a disease or disorder in connection with activity of a uric acid transporter 1 (URAT1) protein.

In another aspect, the present invention provides methods of treating or delaying the progression or onset of a disease or disorder in connection with activity of a uric acid transport 1 (URAT1) protein, comprising administering to a subject in need thereof a pharmaceutical composition comprising any of crystalline forms of lesinurad salts selected from calcium salt, potassium salt, hydrochloride, esylate, mesylate, 1,2-ethanedisulfonate, isethionate, arginine salt and co-crystal composing lesinurad and a co-crystal former selected from proline and glycolic acid, or any of combinations thereof.

In another aspect, the present invention provides a kit for the treatment of a disease or disorder in connection with activity of a URAT1 protein, comprising a pharmaceutical composition comprising any of crystalline forms of lesinurad salts selected from calcium salt, potassium salt, hydrochloride, esylate, mesylate, 1,2-ethanedisulfonate, isethionate, arginine salt and co-crystal composing lesinurad and a co-crystal former selected from proline and glycolic acid, or any of combinations thereof, in a container and, optionally, instructions describing use.

Other aspects and embodiments of the present invention will be further illustrated in the following description and examples.

DETAILED DESCRIPTION OF THE INVENTION

Figure 1:
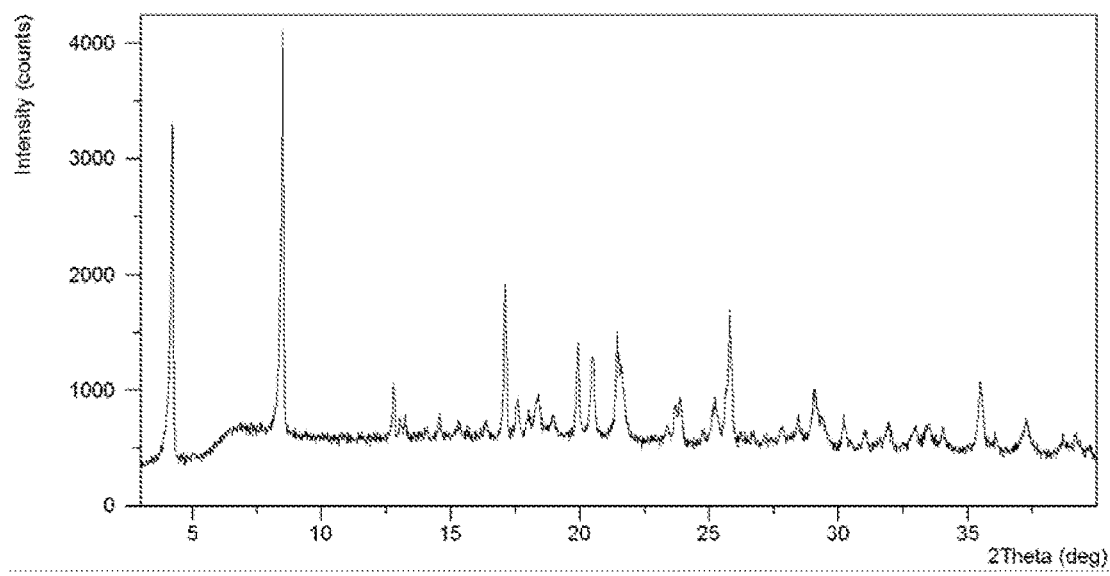
FIG. 1 shows an X-ray powder diffraction (XRPD) pattern of calcium salt Form A.

The present invention is based on a surprising discovery that lesinurad can exist in different crystallization salts and co-crystals, and these salts and co-crystals can be prepared readily from environmentally friendly solvent systems using relatively simple processes.

In one aspect, the present invention provides lesinurad salts selected from calcium salt, potassium salt, hydrochloride, esylate, mesylate, 1,2-ethanedisulfonate, isethionate, and arginine salts.

In another aspect, said salt of the compound of Formula (I) is in a crystalline form selected from calcium salt Form A, potassium salt Form A, hydrochloride Form A, hydrochloride Form B, esylate Form A, mesylate Form A, mesylate Form B, 1,2-ethanedisulfonate Form A, 1,2-ethanedisulfonate Form B, isethionate Form A, arginine salt Form A.

In another aspect, the present invention provides a co-crystal composing lesinurad and a co-crystal former. The co-crystal former is selected from proline and glycolic acid.

In one embodiment, the salts and co-crystals of the compound of Formula (I) are characterized by X-ray powder diffraction patterns with specific peaks at about 2-theta as shown in Table 1.

TABLE 1

Primary Reflections distinguishing novel forms from compound of Formula (I) salts and co-crystals

| Salt/co-crystal | Crystalline form | Angle (°2θ) |
| --- | --- | --- |
| calcium salt | A | 8.5°, 4.2°, 17.1° |
| potassium salt | A | 23.8°, 11.8°, 23.1° |
| hydrochloride | A | 10.6°, 20.2°, 9.2° |
| hydrochloride | B | 23.8°, 21.4°, 23.0° |

TABLE 1-continued

Primary Reflections distinguishing novel forms from compound of Formula (I) salts and co-crystals

| Salt/co-crystal | Crystalline form | Angle (°2θ) |
|---|---|---|
| esylate | A | 21.8°, 21.6°, 18.8° |
| mesylate | A | 23.8°, 18.6°, 6.1° |
| mesylate | B | 7.2°, 22.4°, 5.7° |
| 1,2-ethanedisulfonate | A | 21.9°, 9.4°, 15.7° |
| 1,2-ethanedisulfonate | B | 17.6°, 11.8°, 21.5° |
| isethionate | A | 6.0°, 18.2°, 23.4° |
| arginine salt | A | 8.9°, 17.3°, 5.9° |
| co-crystal | lesinurad and proline | 21.9°, 18.1°, 20.2° |
| co-crystal | lesinurad and glycolic acid | 21.3°, 20.9°, 17.9° | wherein the 2-theta values may vary by ±0.2°.

In another embodiment, the salts of the compound of Formula (I) are characterized by X-ray powder diffraction patterns with specific peaks (in addition to those in Table 1) at about 2-theta as shown in Table 2.

TABLE 2

Secondary Reflections distinguishing novel forms from compound of Formula (I) salts

| Salt | Crystalline form | Angle (°2θ) |
|---|---|---|
| calcium salt | A | 19.9°, 20.5°, 21.4°, 23.8°, 25.1°, 25.8°, 29.0° |
| potassium salt | A | 17.2°, 26.1°, 25.0°, 21.8°, 26.8°, 7.3°, 27.6° |
| hydrochloride | A | 23.0°, 25.9°, 25.4°, 22.2°, 6.9°, 17.9°, 24.5° |
| hydrochloride | B | 26.7°, 23.4°, 10.5°, 18.4°, 24.6°, 30.0°, 31.1° |
| esylate | A | 5.7°, 25.5°, 19.7°, 8.7°, 14.9°, 24.1°, 29.5° |
| mesylate | A | 23.3°, 9.4°, 24.3°, 12.5°, 17.5°, 18.8°, 22.3° |
| mesylate | B | 8.9°, 23.7°, 17.2°, 17.9°, 15.8°, 19.6°, 26.2° |
| 1,2-ethanedisulfonate | A | 18.6°, 19.1°, 20.9°, 29.5°, 5.1°, 23.9°, 26.8° |
| 1,2-ethanedisulfonate | B | 22.7°, 5.8°, 21.8°, 23.5°, 25.2°, 27.1°, 28.7° |
| isethionate | A | 22.8°, 24.4°, 23.8°, 12.4°, 21.8°, 15.0°, 25.7° |
| arginine salt | A | 24.5°, 22.9°, 23.5°, 21.5°, 19.3°, 14.6°, 26.9° |
| co-crystal | lesinurad and proline | 12.6°, 13.1°, 14.8°, 18.9°, 19.8°, 20.5°, 24.8° |
| co-crystal | lesinurad and glycolic acid | 10.9°, 11.4°, 13.0°, 17.4°, 24.3°, 25.4°, 27.3° | wherein the 2-theta values may vary by ±0.2°.

In another aspect, the present invention provides processes for preparing salts or co-crystals, comprising crystallizing lesinurad with salt or co-crystal formers in one or two crystallization solvents selected from organic solvents and mixtures of organic solvent and water.

In one embodiment, the organic solvent is an alcoholic solvent, alkylketene solvent, ether solvent, ester solvent, or acetonitrile. In another embodiment, the alcoholic solvent is methanol; the alkylketene solvent is acetone; the ether solvent is tetrahydrofuran; and the ester solvent is ethyl acetate.

In one embodiment, the solution is stirred to precipitate the salt or co-crystal. In another embodiment, the solution is cooled to precipitate the salt or co-crystal.

In another aspect, the present invention provides solid pharmaceutical compositions, comprising, as an active ingredient, any one or combination of the crystalline forms of lesinurad salts and/or lesinurad cocrystals described herein.

Crystalline forms of lesinurad salts and/or lesinurad cocrystals, together with one or more pharmaceutically acceptable excipients, of the present invention may be further formulated as: solid oral dosage forms such as, but not limited to, powders, granules, pellets, tablets, and capsules; liquid oral dosage forms such as, but not limited to, syrups, suspensions, dispersions, and emulsions; and injectable preparations such as, but not limited to, solutions, dispersions, and freeze dried compositions. Formulations may be in the forms of immediate release, delayed release or modified release. Further, immediate release compositions may be conventional, dispersible, chewable, mouth dissolving, or flash melt preparations; and modified release compositions may comprise hydrophilic or hydrophobic, or combinations of hydrophilic and hydrophobic, release rate controlling substances to form matrix or reservoir, or combination of matrix and reservoir systems. The compositions may be prepared using techniques such as direct blending, dry granulation, wet granulation, and extrusion and spheronization. Compositions may be presented as uncoated, film coated, sugarcoated, powder coated, enteric coated, or modified release coated.

In another aspect, the present invention provides methods of using crystalline forms of lesinurad salts and/or lesinurad cocrystals, in the manufacture of a medicament for treating or delaying the progression or onset of a disease or disorder in connection with activity of a URAT1 protein.

In another aspect, the present invention provides methods of treating or delaying the progression or onset of a disease or disorder in connection with activity of a URAT1 protein, comprising administering to a subject in need thereof a pharmaceutical composition comprising crystalline forms of lesinurad salts and/or lesinurad cocrystals.

In another aspect the present invention provides kits for the treatment of diseases and disorders, such as the ones described herein. These kits comprise any of the crystal forms of lesinurad salts and/or lesinurad cocrystals, or combination or pharmaceutical composition thereof in a container and, optionally, instructions describing the use of the kit according to the various methods described herein. Such kits may also include information, such as scientific literature references, package insert materials, clinical trial results, or the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kits described herein may be used directly by a patient or consumer according to the instructions included therein or according to directions provided by a physician, nurse, or pharmacist, or the like.

The diseases and disorders in connection with the activity of a URAT1 protein, as referred anywhere in this application, include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis, and sarcoidosis. In a preferred embodiment, the disease or disorder is hyperuricaemia, gout, or gouty arthritis.

The term "subject", as used herein, refers to a mammalian or non-mammalian animal. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment of the methods and compositions provided herein, the mammalian animal is a human. In another embodiment, the mammalian animal is a domestic animal, such as a dog, cat, or horse.

The terms "effective amount", "therapeutically effective amount" or the like, as used herein, refer to an amount of any of the crystalline forms of lesinurad or its sodium salt being administered that is sufficient to cause biologically or clinically significant effect on a subject in the treatment or prevention of a particular disease or condition. The result can be reduction and/or alleviation of the signs, symptoms, or causes of a disease, or any other desired alteration of a biological system. For example, an "effective amount" for therapeutic uses is the amount of the composition comprising a crystal form as disclosed herein required to provide a clinically significant decrease in a disease. An appropriate "effective" amount in any individual case may be determined using techniques known to a person skilled in the art.

The term "substantially," when referring to a characteristic figure of a crystal form, as used herein, refers to a powder x-ray diffraction pattern or differential scanning calorimetry pattern, or the like, that may be non-identical to those depicted herein, but that falls within the limits of experimental error and thus may be deemed as derived from the same crystal form as disclosed herein, as judged by a person of ordinary skill in the art.

EXAMPLES

X-Ray Powder Diffraction (XRPD)

Analytical Instrument: Panalytical Empyrean. The X-ray powder diffractogram was determined by mounting a sample of the crystalline material on a Si single crystal low-background holder and spreading out the sample into a thin layer with the aid of a microscope slide. The 2θ position was calibrated against Panalytical 640 Si powder standard. The sample irradiated with X-rays generated by a copper long-fine focus tube operated at 45 kV and 40 mA with a wavelength of Kα1=1.540589 angstroms and Kα2=1.544426 angstroms (Kα1/Kα2 intensity ratio is 0.50). The collimated X-ray source was passed through a programmed divergence slit set at 10 mm and the reflected radiation directed through a 5.5 mm anti-scattering slit. The sample was exposed for 16.3 seconds per 0.013° 2-theta increment (continuous scan mode) over the range 3 degrees to 40 degrees 2-theta in theta-theta mode. The running time was 3 minutes and 57 seconds. The instrument was equipped with an RTMS detector (X'Celerator). Control and data capture was accomplished by means of a Dell Optiplex 780 XP operating with data collector software.

Persons skilled in the art of X-ray powder diffraction will realize that the relative intensity of peaks can be affected by, for example, grains above 30 microns in size and non-unitary aspect ratios that may affect analysis of samples. The skilled person will also realize that the position of reflections can be affected by the precise height at which the sample sits in the diffractometer and the zero calibration of the diffractometer. The surface planarity of the sample may also have a small effect. Hence, the diffraction pattern data presented are not to be taken as absolute values.

Figure 2:
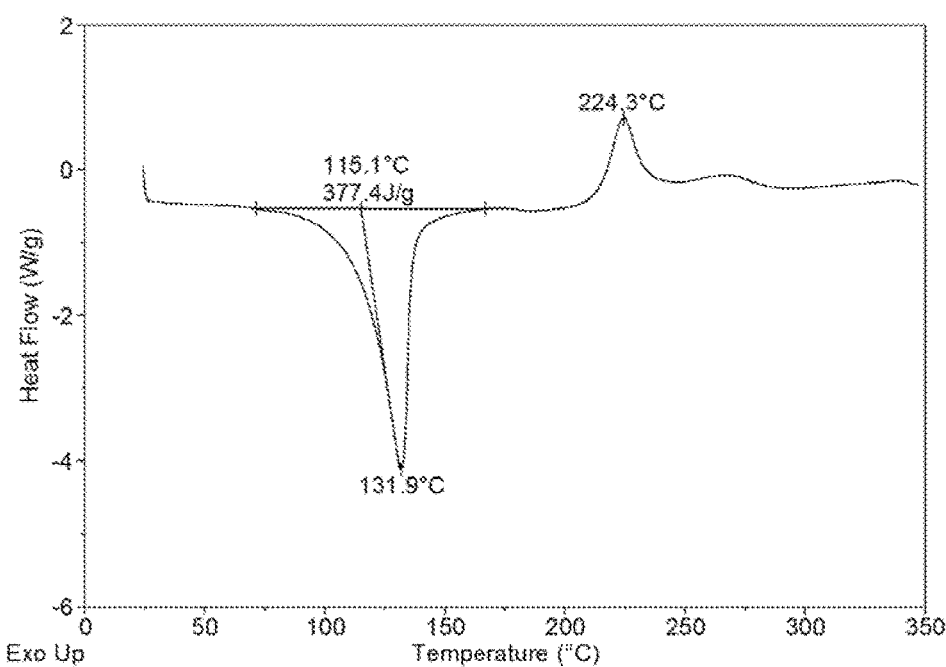
FIG. 2 shows a differential scanning calorimetry (DSC) thermogram of calcium salt Form A.
Figure 3:
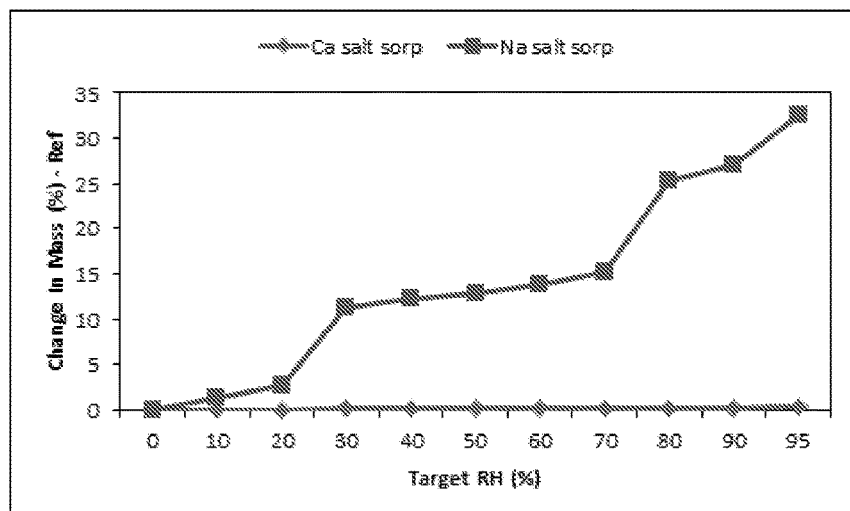
FIG. 3 shows a dynamic vapor sorption (DVS) isotherm plot of calcium salt Form A.

Differential Scanning Calorimetry (DSC)
  Analytical Instrument: TA Instruments Q2000 DSC.
  Heating rate: 10° C. per minute.
  Purge gas: nitrogen
Thermal Gravimetric Analysis (TGA)
  Analytical Instrument: TA Instruments Q500 TGA.
  Heating rate: 10° C. per minute.
  Purge gas: nitrogen.
Dynamic Vapor Sorption (DVS)
  Dynamic Vapor Sorption (DVS) was measured via a SMS (Surface Measurement Systems) DVS Intrinsic. The relative humidity at 25° C. was calibrated against deliquescence point of LiCl, $Mg(NO_3)_2$ and KCl. Typical Parameters for DVS test are listed below.
  Temperature: 25° C.
  Gas and flow rate: $N_2$, 200 mL/min
  dm/dt: 0.002%/min
  RH range: 0% RH to 95% RH Example 1. Preparation of Lesinurad Calcium Salt Form A In 2.0 mL of tetrahydrofuran/water (19:1, v/v) was dissolved 151.1 mg of lesinurad, followed by the addition of 14.2 mg of calcium hydroxide. The mixture was stirred under ambient conditions for 24 hours. The solid was isolated by centrifugation and lesinurad calcium salt Form A was produced, which was analyzed by XRPD, DSC, TGA and DVS. The XRPD pattern, DSC thermogram and DVS isotherm plot of lesinurad calcium salt Form A obtained from this example are displayed in FIGS. 1-3, respectively.

The calcium salt Form A has a DSC thermogram comprising an endothermic peak with onset temperature of about 115.1° C., and a TGA thermogram comprising about 11.4% weight loss up to 110° C.

Figure 4:
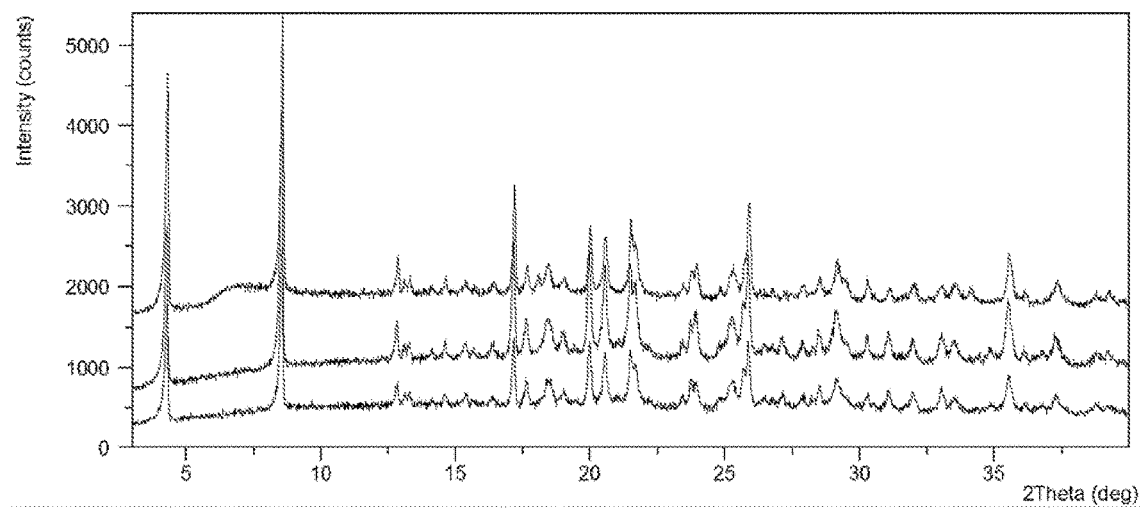
FIG. 4 shows comparison of the XRPD pattern of calcium salt Form A before storage (top pattern), the XRPD pattern of calcium salt Form A after being stored under 25° C./60% RH for 14 days (middle pattern) and the XRPD pattern of calcium salt Form A after being stored under 40° C./75% RH for 14 days (bottom pattern).

Example 2. Stability Assessment of Lesinurad Calcium Salt Form A Under Stress Conditions Two samples of lesinurad calcium salt Form A were stored under 25° C./60% RH and 40° C./75% RH, respectively, with dish open for 14 days. The solid samples were analyzed by XRFD. The XRFD patterns of the calcium salt Form A sample before storage (top pattern) and of the calcium salt Form A sample after being stored under 25° C./60% RH for 14 days (middle pattern) and of the calcium salt Form A sample after being stored under 40° C./75% RH for 14 days (bottom pattern) are displayed in FIG. 4. The results of stability assessment tabulated in Table 3 suggest that calcium salt Form A is stable under the stress conditions.

TABLE 3

| Initial form | Conditions | Storage time | Final form |
|---|---|---|---|
| calcium salt Form A (top pattern in FIG. 4) | 25° C./60% RH | 14 days | calcium salt Form A (middle pattern in FIG. 4) |
| calcium salt Form A (top pattern in FIG. 4) | 40° C./75% RH | 14 days | calcium salt Form A (bottom pattern in FIG. 4) |

Example 3. Hygroscopicity Assessment of Lesinurad Calcium Salt Form A

Hygroscopicity of lesinurad calcium salt Form A was investigated using dynamic vapor sorption (DVS). The DVS isotherm plot of lesinurad calcium salt Form A displayed in FIG. 3 and the detailed data listed in Table 4 show that the sample has 0.8% water uptake under 80% RH, 25° C., suggesting calcium salt Form A is almost not hygroscopic, and it does not deliquesce under high humidity conditions.

TABLE 4

| Solid Form | Water uptake under 80% RH | Water uptake under 95% RH |
| --- | --- | --- |
| calcium salt Form A | 0.15% | 0.33% |
| sodium salt Form A (WO2011085009A2) | 25.11% | 32.13% |

Hygroscopicity criteria applied in this example refers to the standard in European pharmacopoeia:
deliquescent: sufficient water is absorbed to form a liquid,
very hygroscopic: increase in mass is equal to or greater than 15 percent,
hygroscopic: increase in mass is less than 15 percent and equal to or greater than 2 percent,
slightly hygroscopic: increase in mass is less than 2 percent and equal to or greater than 0.2 percent.

Example 4. Preparation of Lesinurad Potassium Salt Form A

Figure 5:
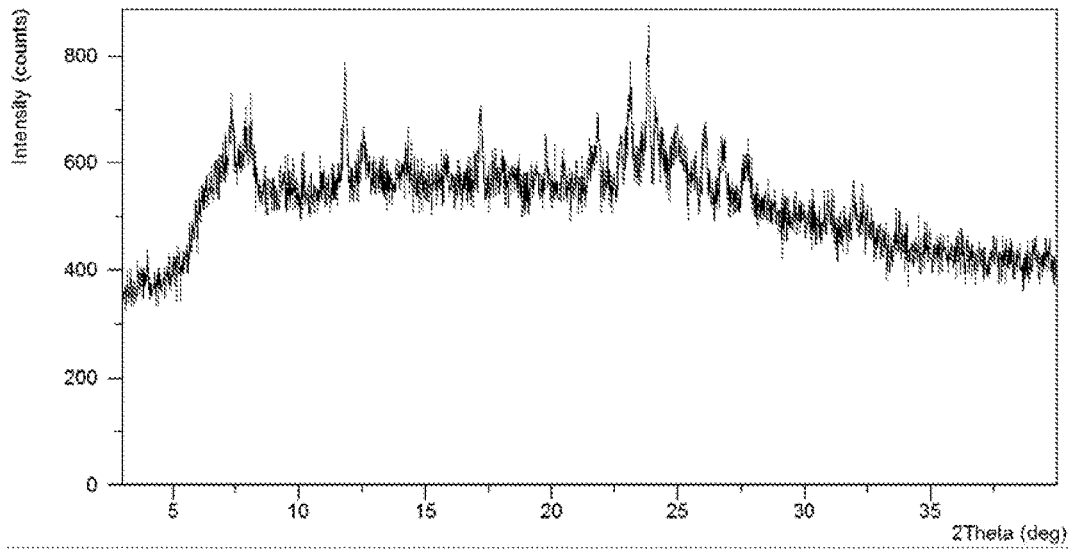
FIG. 5 shows an X-ray powder diffraction (XRPD) pattern of potassium salt Form A.

In 0.6 mL of ethyl acetate was dissolved 10 mg of lesinurad, followed by the addition of 1.9 mg of potassium hydroxide. The mixture was stirred under ambient conditions for 40 hours. The solid was isolated by centrifugation and lesinurad potassium Form A was produced, which was analyzed by XRPD, DSC, and TGA. The XRPD pattern of lesinurad potassium salt Form A obtained from this example is displayed in FIG. 5, respectively.

Potassium salt Form A has a DSC thermogram comprising two endothermic peaks with onset temperature of about 72.7° C. and 135.0° C., and a TGA thermogram comprising about 6.0% weight loss up to 130° C.

Example 5. Preparation of Lesinurad Hydrochloride Form A

Figure 6:
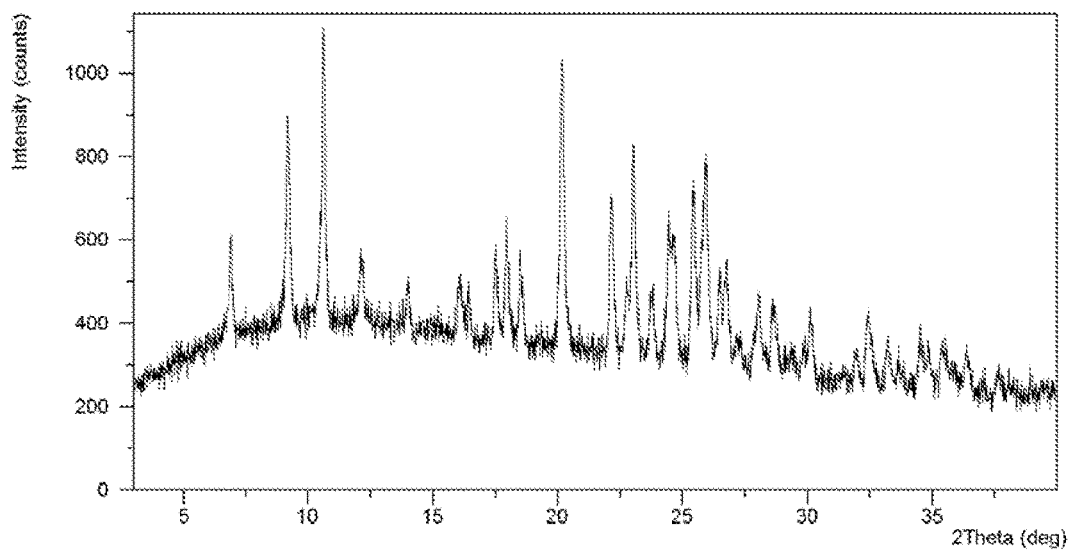
FIG. 6 shows an X-ray powder diffraction (XRPD) pattern of hydrochloride Form A.

In 0.6 mL of ethyl acetate was dissolved 10 mg of lesinurad, followed by the addition of 2.5 µL of hydrochloride solution (36.5 wt %). The solution was stirred under ambient conditions for 40 hours. The solid was centrifuged and the lesinurad hydrochloride Form A was obtained, which was analyzed by XRPD, DSC, and TGA. The XRPD pattern of lesinurad hydrochloride Form A obtained from this example is displayed in FIG. 6, respectively.

Hydrochloride Form A has a DSC thermogram comprising two endothermic peaks with onset temperature of about 122.4° C. and 153.5° C., and a TGA thermogram comprising about 18.2% weight loss up to 153° C.

Example 6. Preparation of Lesinurad Hydrochloride Form B

Figure 7:
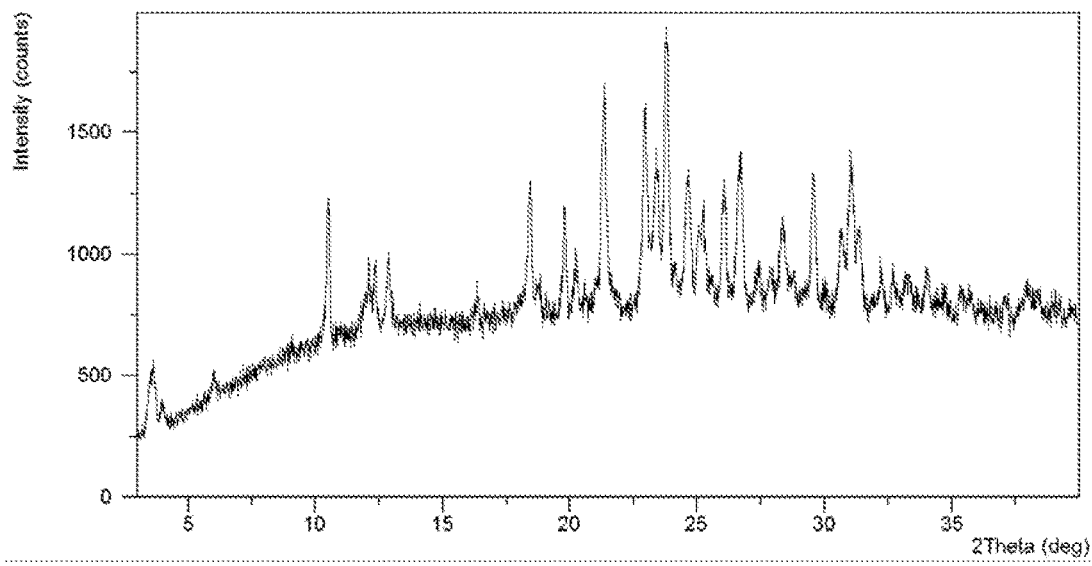
FIG. 7 shows an X-ray powder diffraction (XRPD) pattern of hydrochloride Form B.

In 1.1 mL of ethyl acetate was dissolved 149.9 mg of lesinurad, followed by the addition of 37.7 mg of hydrochloride solution (36.5 wt %). The solution was stirred under ambient conditions for 40 hours. The solid was centrifuged and the lesinurad hydrochloride Form B was obtained, which was analyzed by XRPD, DSC, and TGA. The XRPD pattern of lesinurad calcium salt Form A obtained from this example is displayed in FIG. 7, respectively.

Hydrochloride Form B has a DSC thermogram comprising four endothermic peaks with peak temperature of about 94.1° C., 109.7° C., 155.3° C. and 166.5° C., and a TGA thermogram comprising about 8.2% weight loss up to 140° C.

Example 7. Preparation of Lesinurad Esylate Form A

Figure 8:
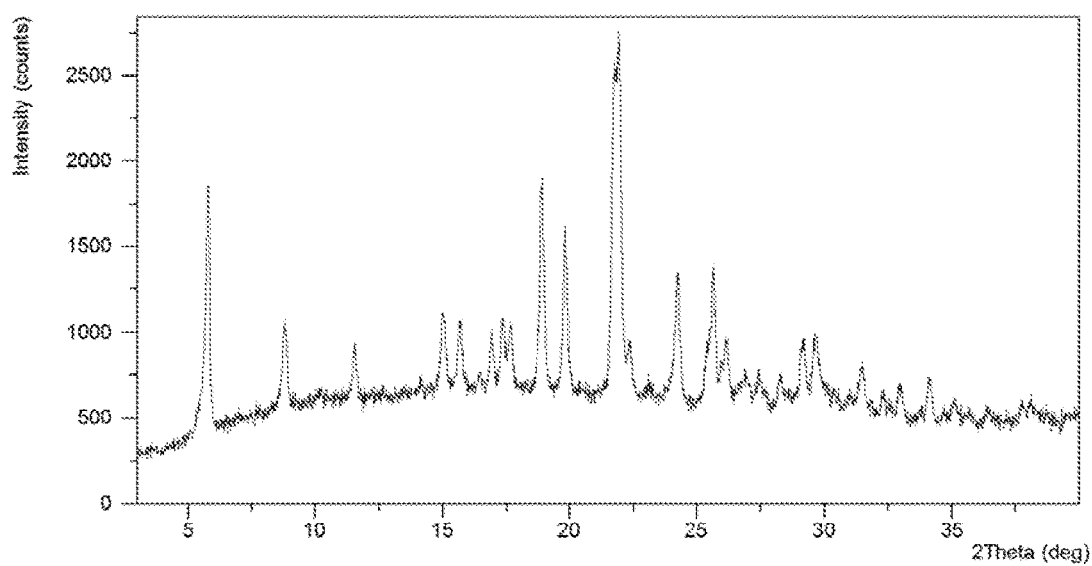
FIG. 8 shows an X-ray powder diffraction (XRPD) pattern of esylate Form A.
Figure 9:
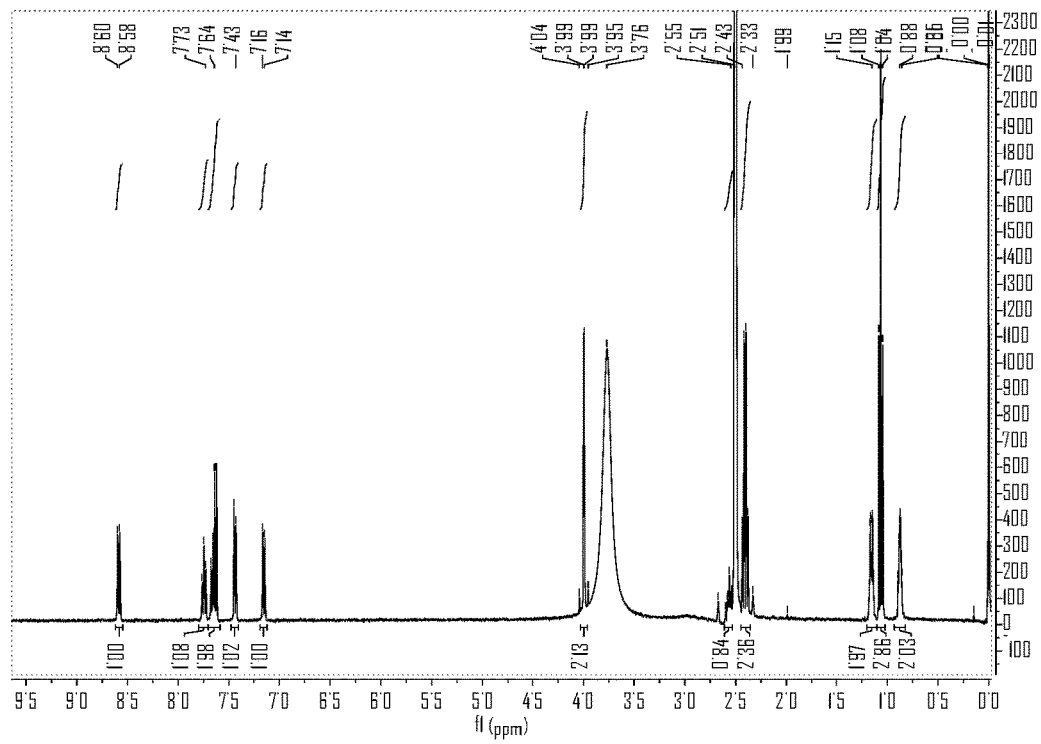
FIG. 9 shows a $^1$H-NMR spectrum of esylate Form A dissolved in DMSO-$d_6$.

In 2.5 mL of ethyl acetate was dissolved 150.5 mg of lesinurad, followed by the addition of 40.5 mg of ethanesulfonic acid. The solution was stirred under ambient conditions for 24 hours. The solid was centrifuged and the lesinurad esylate Form A was obtained, which was analyzed by XRPD, DSC, TGA and NMR. The XRPD pattern, $^1$H-NMR spectrum of lesinurad esylate Form A obtained from this example are displayed in FIGS. 8 and 9, respectively.

Esylate Form A has a DSC thermogram comprising an endothermic peak with onset temperature of about 177.3° C., and a TGA thermogram comprising about 0.9% weight loss up to 140° C.

$^1$H NMR (400 MHz, DMSO) δ 8.59 (d, J=8.5 Hz, 1H), 7.75 (t, J=7.1 Hz, 1H), 7.65 (dd, J=13.9, 7.4 Hz, 2H), 7.44 (d, J=7.6 Hz, 1H), 7.15 (d, J=8.3 Hz, 1H), 3.99 (d, J=1.7 Hz, 2H), 2.56 (td, J=8.5, 4.4 Hz, 1H), 2.40 (q, J=7.4 Hz, 2H), 1.16 (dd, J=8.4, 2.0 Hz, 2H), 1.06 (t, J=7.4 Hz, 3H), 0.87 (dd, J=9.0, 5.4 Hz, 2H).

Example 8. Preparation of Lesinurad Mesylate Form A

Figure 10:
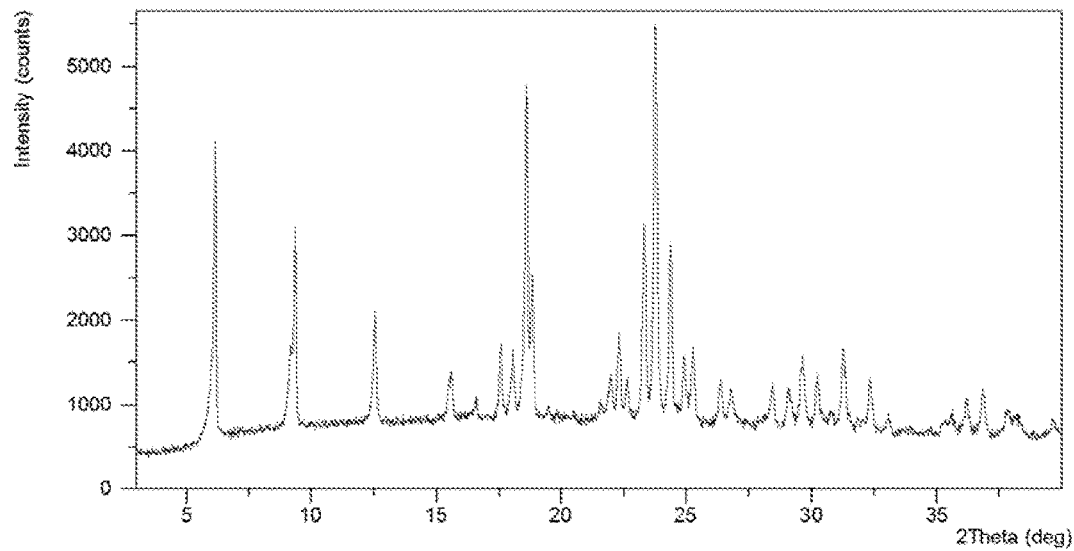
FIG. 10 shows an X-ray powder diffraction (XRPD) pattern of mesylate Form A.
Figure 11:
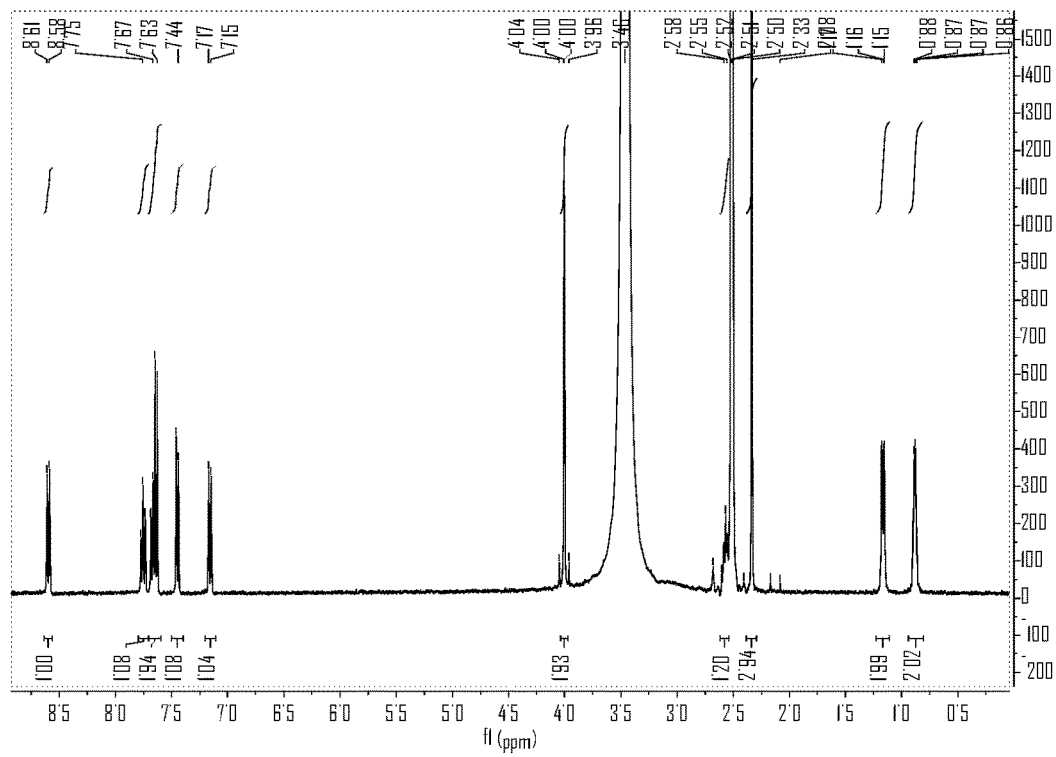
FIG. 11 shows a $^1$H-NMR spectrum of mesylate Form A dissolved in DMSO-$d_6$.

In 2.5 mL of acetonitrile was dissolved 150.1 mg of lesinurad, followed by the addition of 36.7 mg of methanesulfonic acid. The solution was stirred under ambient conditions for 24 hours. The solid was centrifuged and the lesinurad mesylate Form A was obtained, which was analyzed by XRPD, DSC, TGA and NMR. The XRPD pattern, $^1$H-NMR spectrum of lesinurad mesylate Form A obtained from this example are displayed in FIGS. 10 and 11, respectively.

Mesylate Form A has a DSC thermogram comprising an endothermic peak with onset temperature of about 173.2° C., and a TGA thermogram comprising about 0.4% weight loss up to 150° C.

$^1$H NMR (400 MHz, DMSO) δ 8.59 (d, J=8.5 Hz, 1H), 7.75 (dd, J=11.3, 4.1 Hz, 1H), 7.70-7.59 (m, 2H), 7.45 (d, J=7.7 Hz, 1H), 7.16 (d, J=8.2 Hz, 1H), 4.00 (d, J=1.7 Hz, 2H), 2.57 (td, J=8.5, 4.4 Hz, 1H), 2.33 (s, 3H), 1.16 (dd, J=8.4, 2.0 Hz, 2H), 0.94-0.80 (m, 2H).

Example 9. Preparation of Lesinurad Mesylate Form B

Figure 12:
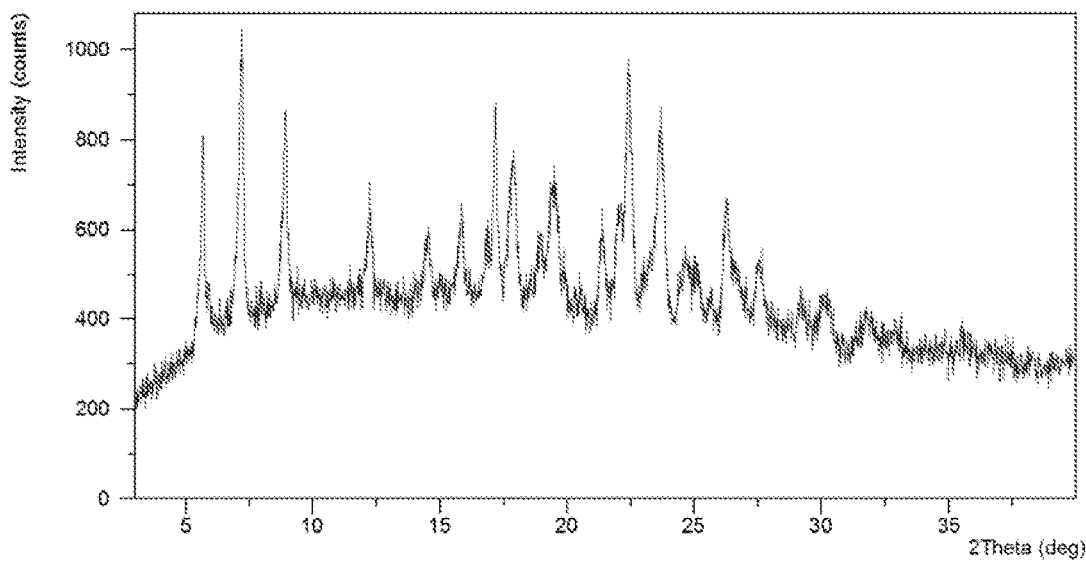
FIG. 12 shows an X-ray powder diffraction (XRPD) pattern of mesylate Form B.
Figure 13:
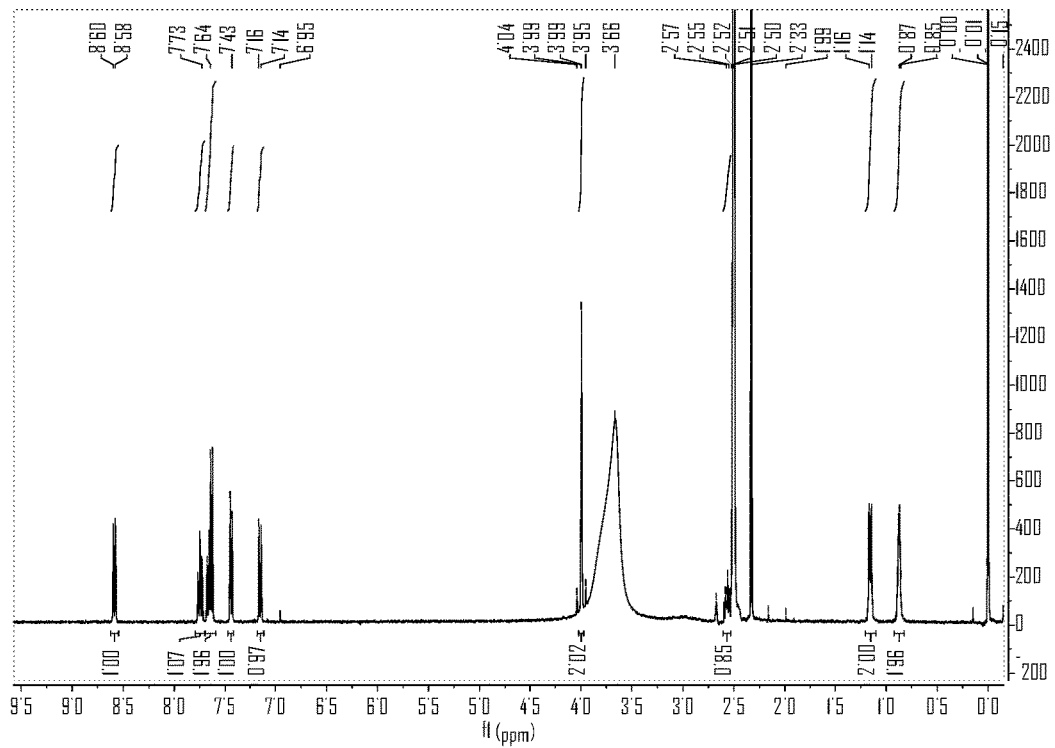
FIG. 13 shows a $^1$H-NMR spectrum of mesylate Form B dissolved in DMSO-$d_6$.

In 0.6 mL of ethyl acetate was dissolved 10.0 mg of lesinurad, followed by the addition of 3.1 mg of methanesulfonic acid. The solution was stirred under ambient conditions for 24 hours. The solid was centrifuged and the lesinurad mesylate Form B was obtained, which was analyzed by XRPD, DSC, TGA and NMR. The XRPD pattern, $^1$H-NMR spectrum of lesinurad mesylate Form B obtained from this example are displayed in FIGS. 12 and 13, respectively.

Mesylate Form B has a DSC thermogram comprising an endothermic peak with onset temperature of about 171.7° C., and a TGA thermogram comprising about 0.9% weight loss up to 150° C.

¹H NMR (400 MHz, DMSO) δ 8.59 (d, J=8.4 Hz, 1H), 7.74 (dd, J=11.3, 4.1 Hz, 1H), 7.65 (dd, J=13.9, 7.4 Hz, 2H), 7.44 (d, J=7.4 Hz, 1H), 7.15 (d, J=8.2 Hz, 1H), 3.99 (d, J=1.7 Hz, 2H), 2.56 (td, J=8.2, 4.1 Hz, 1H), 2.33 (s, 3H), 1.16 (dd, J=8.4, 2.0 Hz, 2H), 0.92-0.82 (m, 2H).

Example 10. Preparation of Lesinurad 1,2-Ethanedisulfonate Form A

Figure 14:
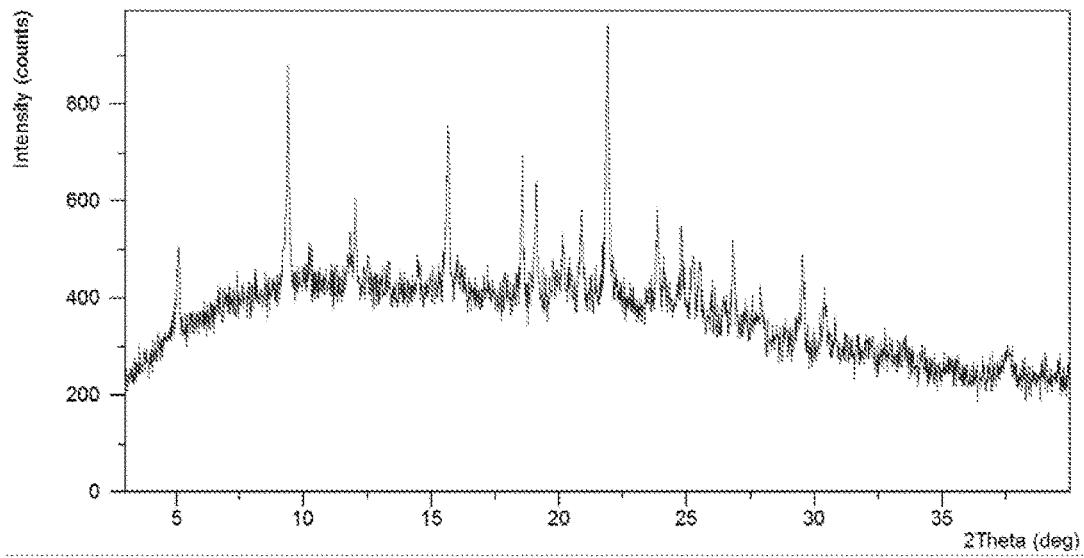
FIG. 14 shows an X-ray powder diffraction (XRPD) pattern of 1,2-ethanedisulfonate Form A.
Figure 15:
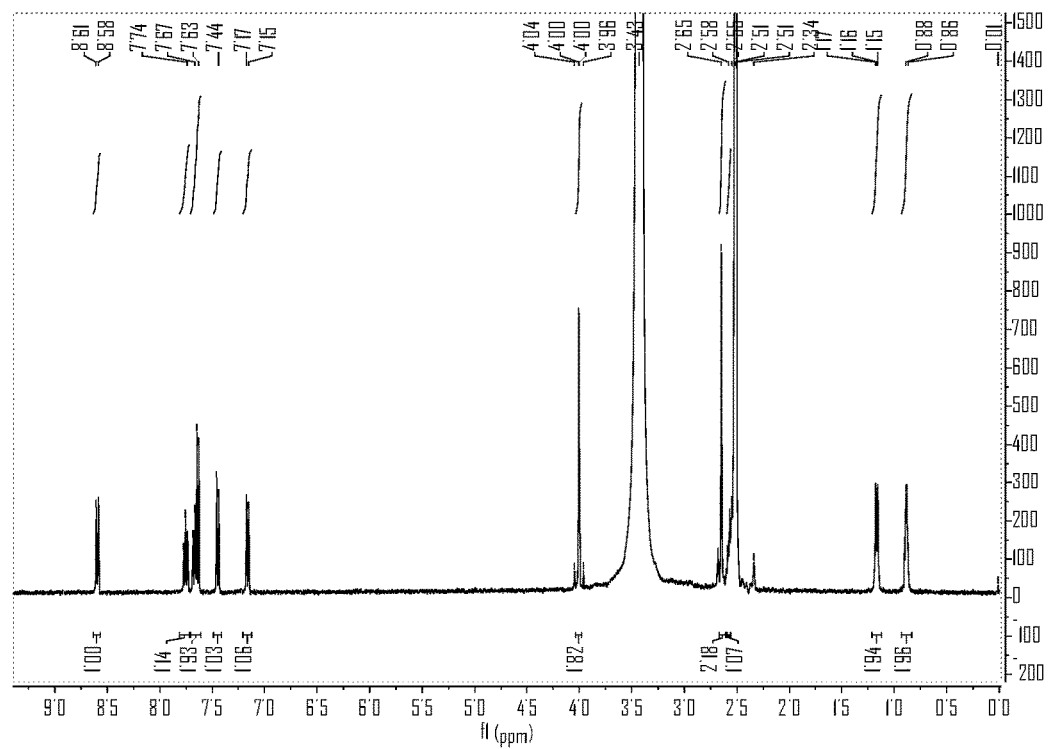
FIG. 15 shows a $^1$H-NMR spectrum of 1,2-ethanedisulfonate Form A dissolved in DMSO-$d_6$.

In 0.4 mL of acetonitrile was dissolved 10.0 mg of lesinurad, followed by the addition of 4.5 mg of 1,2-ethanedisulfonic acid. The solution was stirred under ambient conditions for 24 hours. The solid was centrifuged and the lesinurad 1,2-ethanedisulfonate Form A was obtained, which was analyzed by XRPD, DSC, TGA and NMR. The XRPD pattern, ¹H-NMR spectrum of lesinurad 1,2-ethanedisulfonate Form A obtained from this example are displayed in FIGS. 14 and 15, respectively.

1,2-Ethanedisulfonate Form A has a DSC thermogram comprising an endothermic peak with onset temperature of about 190.6° C., and a TGA thermogram comprising about 1.6% weight loss up to 150° C.

¹H NMR (400 MHz, DMSO) δ 8.59 (d, J=8.5 Hz, 1H), 7.81-7.72 (m, 1H), 7.66 (dd, J=14.4, 7.4 Hz, 2H), 7.45 (d, J=7.7 Hz, 1H), 7.16 (d, J=8.2 Hz, 1H), 4.00 (d, J=1.7 Hz, 2H), 2.65 (s, 2H), 2.59-2.56 (m, 1H), 1.16 (dd, J=8.4, 2.0 Hz, 2H), 0.88 (dd, J=9.0, 5.4 Hz, 2H). The ¹H NMR spectrum indicates that the mole ratio between lesinurad and 1,2-ethanedisulfonic acid is about 2:1, i.e., the salt is a hemi-1,2-ethanedisulfonate salt.

Example 11. Preparation of Lesinurad 1,2-Ethanedisulfonate Form B

Figure 16:
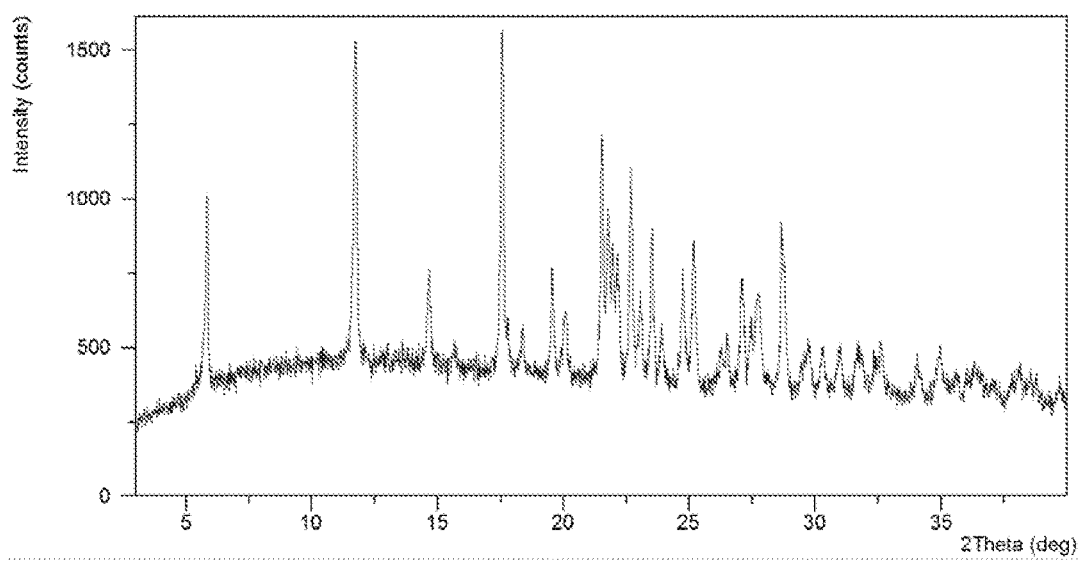
FIG. 16 shows an X-ray powder diffraction (XRPD) pattern of 1,2-ethanedisulfonate Form B.
Figure 17:
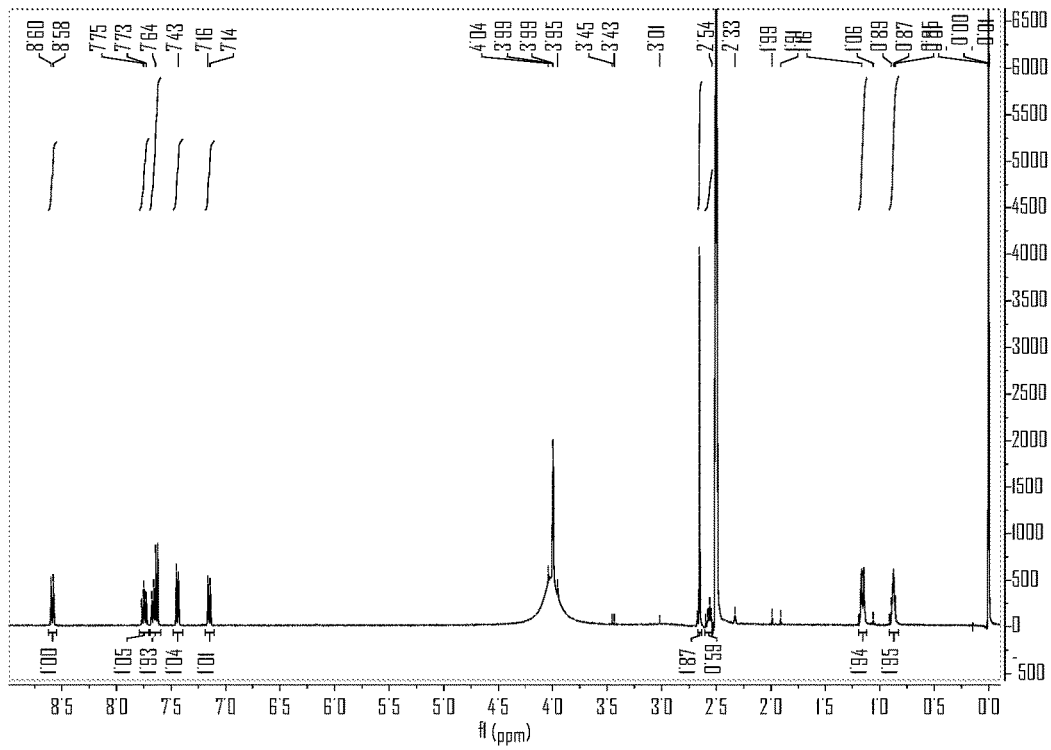
FIG. 17 shows a $^1$H-NMR spectrum of 1,2-ethanedisulfonate Form B dissolved in DMSO-$d_6$.

In 0.6 mL of ethyl acetate was dissolved 10.0 mg of lesinurad, followed by the addition of 4.6 mg of 1,2-ethanedisulfonic acid. The solution was stirred under ambient conditions for 24 hours. The solid was centrifuged and the lesinurad 1,2-ethanedisulfonate Form B was obtained, which was analyzed by XRPD, DSC, TGA and NMR. The XRPD pattern, ¹H-NMR spectrum of lesinurad 1,2-ethanedisulfonate Form B obtained from this example are displayed in FIGS. 16 and 17, respectively.

1,2-Ethanedisulfonate Form B has a DSC thermogram comprising an endothermic peak with onset temperature of about 194.2° C., and a TGA thermogram comprising about 0.5% weight loss up to 160° C.

¹H NMR (400 MHz, DMSO) δ 8.59 (d, J=8.4 Hz, 1H), 7.79-7.70 (m, 1H), 7.65 (dd, J=13.9, 7.4 Hz, 2H), 7.44 (d, J=7.7 Hz, 1H), 7.15 (d, J=8.1 Hz, 1H), 4.00 (d, J=1.7 Hz, 2H), 2.66 (d, J=5.5 Hz, 2H), 2.56 (td, J=8.6, 4.5 Hz, 1H), 1.19-1.11 (m, 2H), 0.91-0.82 (m, 2H).

Example 12. Preparation of Lesinurad Isethionate Form A

Figure 18:
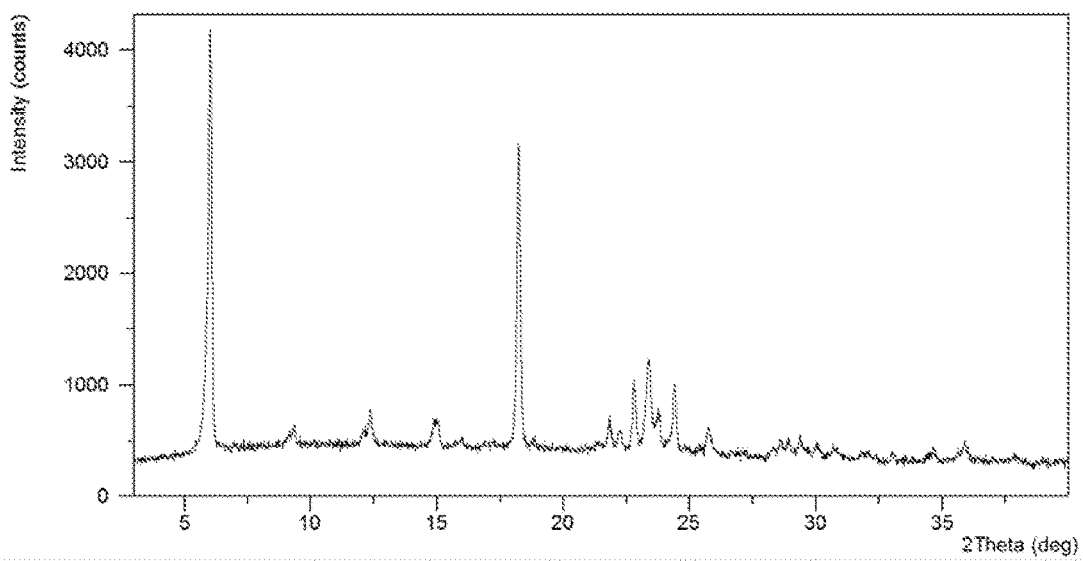
FIG. 18 shows an X-ray powder diffraction (XRPD) pattern of isethionate Form A.
Figure 19:
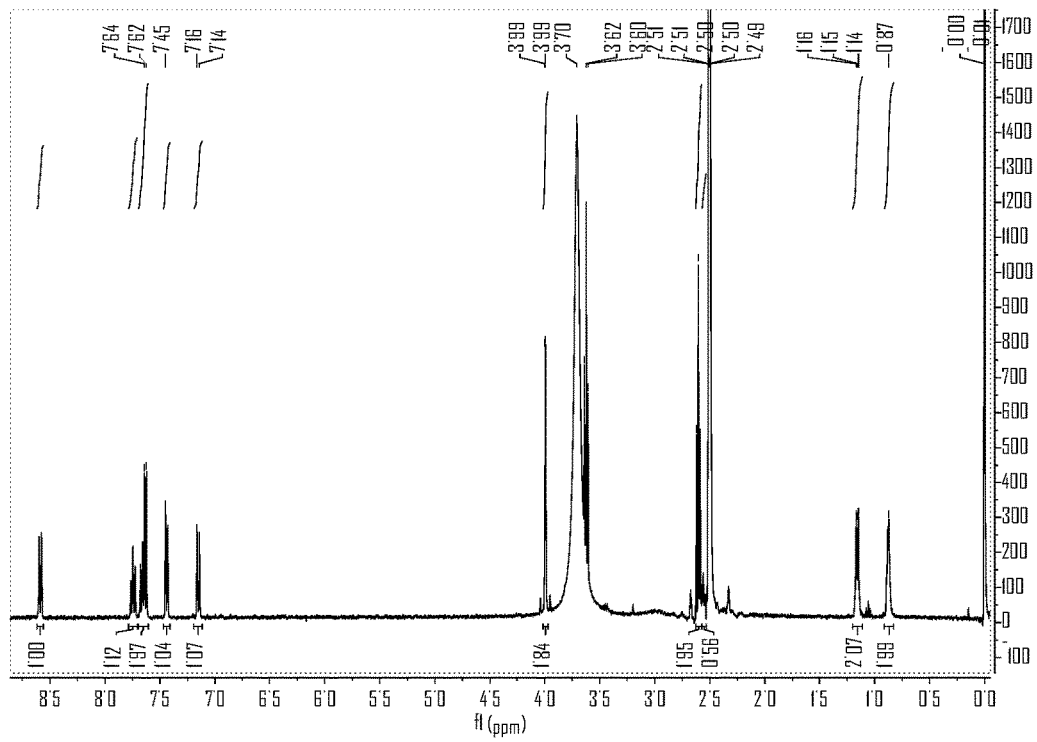
FIG. 19 shows a $^1$H-NMR spectrum of isethionate Form A dissolved in DMSO-$d_6$.

In 0.6 mL of ethyl acetate was dissolved 10.0 mg of lesinurad was added, followed by the addition of 3.9 mg of isethionic acid solution (80 wt %). The solution was stirred under ambient conditions for 24 hours. The solid was centrifuged and the lesinurad isethionate Form A was obtained, which was analyzed by XRPD, DSC, TGA and NMR. The XRPD pattern, ¹H-NMR spectrum of lesinurad isethionate Form A obtained from this example are displayed in FIGS. 18 and 19, respectively.

Isethionate Form A has a DSC thermogram comprising an endothermic peak with onset temperature of about 135.8° C., and a TGA thermogram comprising about 1.9% weight loss up to 110° C.

¹H NMR (400 MHz, DMSO) δ 8.59 (d, J=8.4 Hz, 1H), 7.74 (dd, J=11.3, 4.1 Hz, 1H), 7.63 (dd, J=7.5 Hz, 2H), 7.45 (s, 1H), 7.15 (d, J=8.2 Hz, 1H), 3.99 (d, J=1.7 Hz, 2H), 3.62 (t, 6.7 Hz, 2H), 2.60 (t, J=6.7 Hz, 2H), 2.57-2.53 (m, 1H), 1.20-1.11 (m, 2H), 0.87 (s, 2H). The ¹H NMR spectrum indicates that the mole ratio between lesinurad and isethionic acid is about 1:1.

Example 13. Preparation of Lesinurad Arginine Salt Form A

Figure 20:
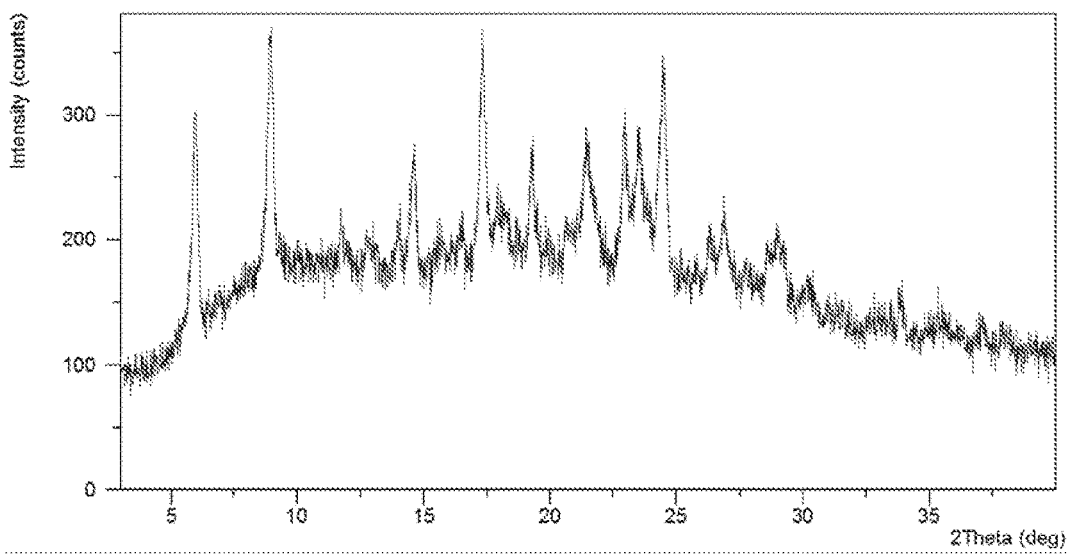
FIG. 20 shows an X-ray powder diffraction (XRPD) pattern of arginine salt Form A.
Figure 21:
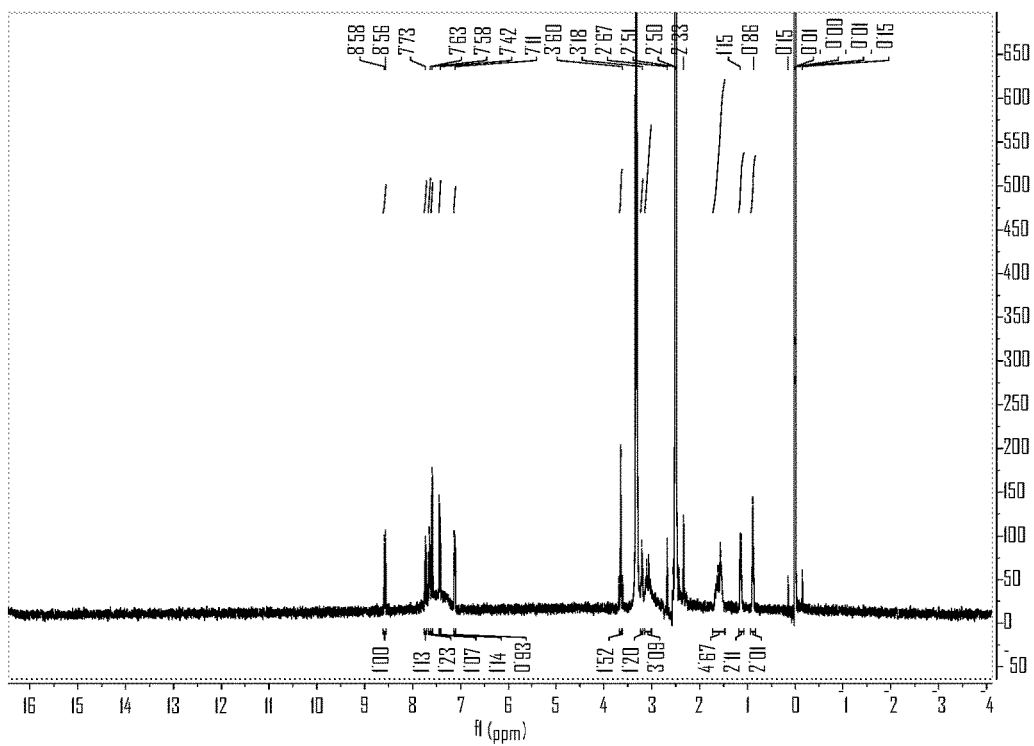
FIG. 21 shows a $^1$H-NMR spectrum of arginine salt Form A dissolved in DMSO-$d_6$.

In 0.4 mL of acetonitrile was dissolved 10 mg of Lesinurad, followed by the addition of 4.3 mg of Arginine. The mixture was stirred under ambient conditions for 24 hours. The solid was centrifuged and lesinurad Arginine salt Form A was produced, which was analyzed by XRPD, DSC, TGA and NMR. The XRPD pattern, ¹H-NMR spectrum of lesinurad isethionate Form A obtained from this example are displayed in FIGS. 20 and 21, respectively.

Arginine salt Form A has a DSC thermogram comprising two endothermic peaks with onset temperature of about 50.2° C. and 182.2° C., and a TGA thermogram comprising about 2.5% weight loss up to 150° C.

¹H NMR (400 MHz, DMSO) δ 8.57 (d, J=8.5 Hz, 1H), 7.75-7.70 (m, 1H), 7.67-7.62 (m, 1H), 7.59 (d, J=7.6 Hz, 1H), 7.43 (d, J=8.0 Hz, 1H), 7.12 (d, J=8.0 Hz, 1H), 3.64 (d, J=3.9 Hz, 2H), 3.19 (d, J=6.9 Hz, 1H), 3.08 (d, J=17.3 Hz, 3H), 1.72-1.47 (m, 5H), 1.14 (d, J=7.8 Hz, 2H), 0.93-0.83 (m, 2H).

Example 14. Preparation of Co-Crystal Composing Lesinurad and Proline

Figure 22:
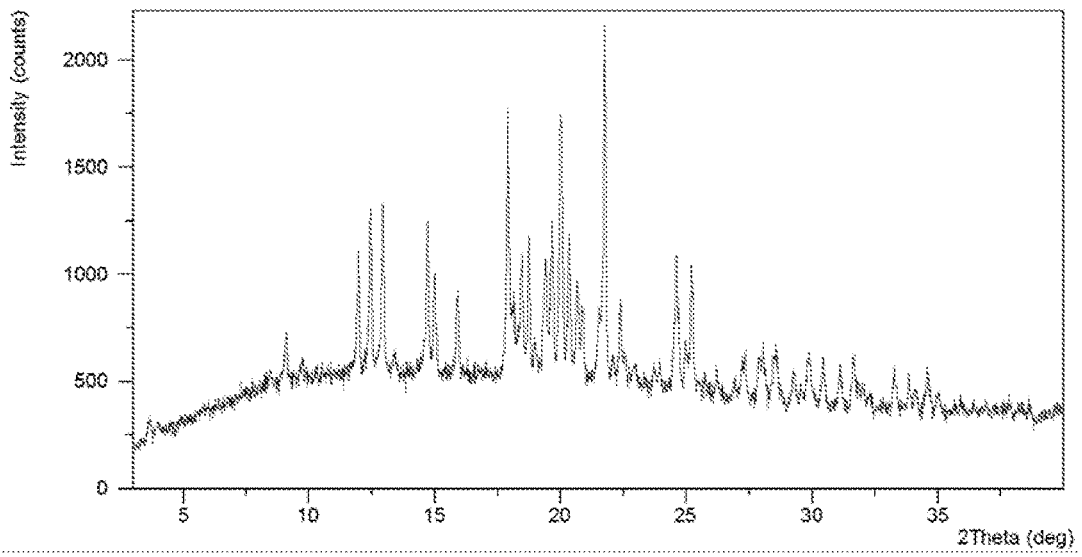
FIG. 22 shows an X-ray powder diffraction (XRPD) pattern of co-crystal composing lesinurad and proline.
Figure 23:
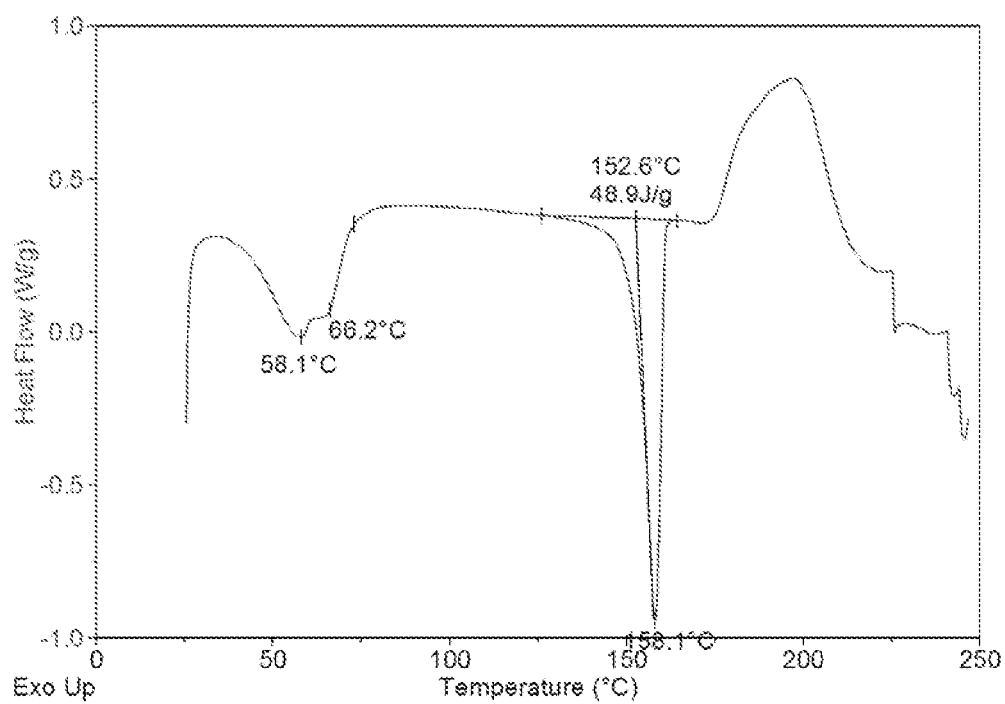
FIG. 23 shows a differential scanning calorimetry (DSC) thermogram of co-crystal composing lesinurad and proline.
Figure 24:
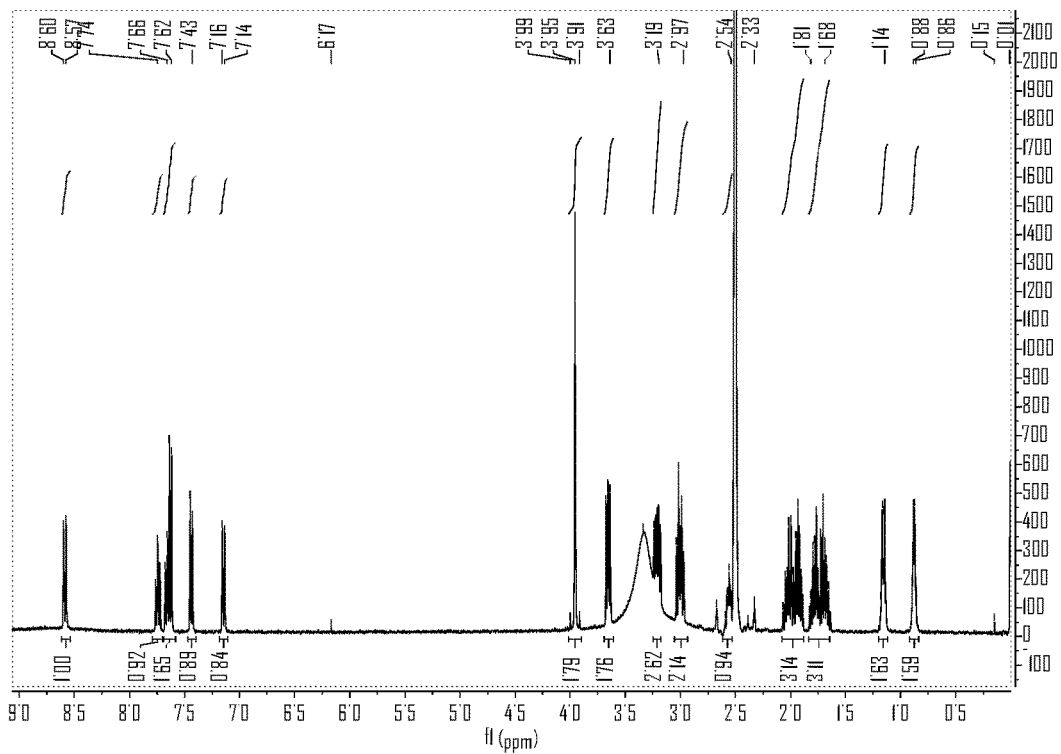
FIG. 24 shows a $^1$H-NMR spectrum of co-crystal composing lesinurad and proline dissolved in DMSO-$d_6$.

To 1.0 mL of ethyl acetate was added 151.2 mg of lesinurad, followed by the addition of 84.4 mg of proline. The mixture was stirred under ambient conditions for 24 h. The suspension was centrifuged and co-crystal composing lesinurad and proline was obtained, which was analyzed by XRPD, DSC, TGA and NMR. The XRPD pattern, DSC thermogram, ¹H-NMR spectrum of co-crystal obtained from this example are displayed in FIGS. 22-24, respectively.

Co-crystal composing lesinurad and proline has a DSC thermogram comprising three endothermic peaks with onset temperature of about 58.1° C., 66.2° C. and 152.6° C., and a TGA thermogram comprising about 2.8% weight loss up to 85° C.

¹H NMR (400 MHz, DMSO) δ 8.58 (d, J=8.5 Hz, 1H), 7.74 (dd, J=11.3, 4.1 Hz, 1H), 7.65 (dd, J=14.9, 7.5 Hz, 2H), 7.44 (d, J=7.5 Hz, 1H), 7.15 (d, J=8.3 Hz, 1H), 4.01-3.89 (m, 2H), 3.65 (dd, J=8.7, 5.7 Hz, 2H), 3.24-3.17 (m, 2H), 3.00 (dt, J=11.2, 7.6 Hz, 2H), 2.56 (td, J=8.3, 4.3 Hz, 1H), 2.07-1.88 (m, 4H), 1.83-1.64 (m, 4H), 1.20-1.11 (m, 2H), 0.87 (q, J=5.4 Hz, 2H). The ¹H NMR spectrum indicates that the mole ratio between lesinurad and proline is about 1:1.

Figure 25:
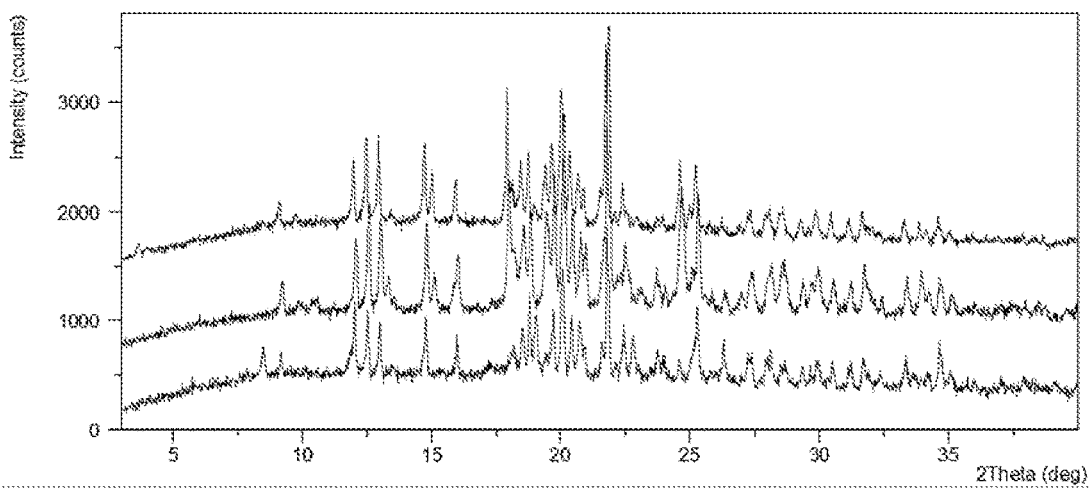
FIG. 25 shows comparison of the XRPD pattern of co-crystal composing lesinurad and proline before storage (top pattern), the XRPD pattern of co-crystal composing lesinurad and proline after being stored under 25° C./60% RH for 14 days (middle pattern) and the XRPD pattern of co-crystal composing lesinurad and proline after being stored under 40° C./75% RH for 14 days (bottom pattern).

Example 15. Stability Assessment of Co-Crystal Composing Lesinurad and Proline Under Stress Conditions Two samples of co-crystal composing lesinurad and proline were stored under 25° C./60% RH and 40° C./75% RH, respectively for 14 days. The solid samples were analyzed by XRPD. The)(RFD patterns of the co-crystal sample before storage (top pattern) and after being stored under 25° C./60% RH for 14 days (middle pattern) and being after stored under 40° C./75% RH for 14 days (bottom pattern) are displayed in FIG. 25. The results of stability assessment tabulated in Table 5 suggest that co-crystal composing lesinurad and proline is stable under stress conditions.

TABLE 5

| Initial form | Conditions | Storage time | Final form |
| --- | --- | --- | --- |
| co-crystal composing lesinurad and proline (top pattern in FIG. 25) | 25° C./60% RH | 14 days | co-crystal composing lesinurad and proline (middle pattern in FIG. 25) |
| co-crystal composing lesinurad and proline (top pattern in FIG. 25) | 40° C./75% RH | 14 days | co-crystal composing lesinurad and proline (bottom pattern in FIG. 25) |

Example 16. Kinetic Solubility Comparison Between Co-Crystal Composing Lesinurad and Proline and Lesinurad Free Acid Kinetic solubility of co-crystal composing lesinurad and proline and lesinurad freeacid in fed state simulated intestinal fluid (FeSSIF) and fasted state simulated intestinal fluid (FaSSIF) were measured using the following procedures:

1. Weigh approximately 30 mg of co-crystal composing lesinurad and proline and lesinurad freeacid into a tared 4-mL plastic vial and record the actual weight of the compound.
2. Add 3 mL of bio-relevant medium into each vial.
3. Cap the vials and keep all the suspension samples stirring at RT (room temperature) using a rolling incubator at a rate of 25 r/min.
4. Sample at 1 h, 4 h and 24 h respectively. About 0.6 mL aliquot of the suspension is transferred per time from solubility vial into a centrifuge filtration tube (pore size of 0.45 μm).
5. Centrifuge filtration tubes at a rate of 8500 rpm for 3 minutes at RT, collect 0.2 mL of supernatant for HPLC quantification determination and collect the rest of solution for pH measurement, and separate the solid for XRPD characterization.

The results displayed in Table 6 suggest co-crystal composing lesinurad and proline has higher solubility in comparison to lesinurad freeacid.

TABLE 6

| | Time point (h) | FaSSIF | | FeSSIF | |
| --- | --- | --- | --- | --- | --- |
| | | lesinurad freeacid | co-crystal composing lesinurad and proline | lesinurad freeacid | co-crystal composing lesinurad and proline |
| Solubility (mg/mL) | 1 | 2.89 | 4.91 | 1.5052 | >10 |
| | 4 | 3.58 | 7.39 | 2.1394 | >10 |
| | 24 | 3.00 | 6.24 | 1.9323 | >10 |

Example 17. Preparation of Co-Crystal Composing Lesinurad and Glycolic Acid

Figure 26:
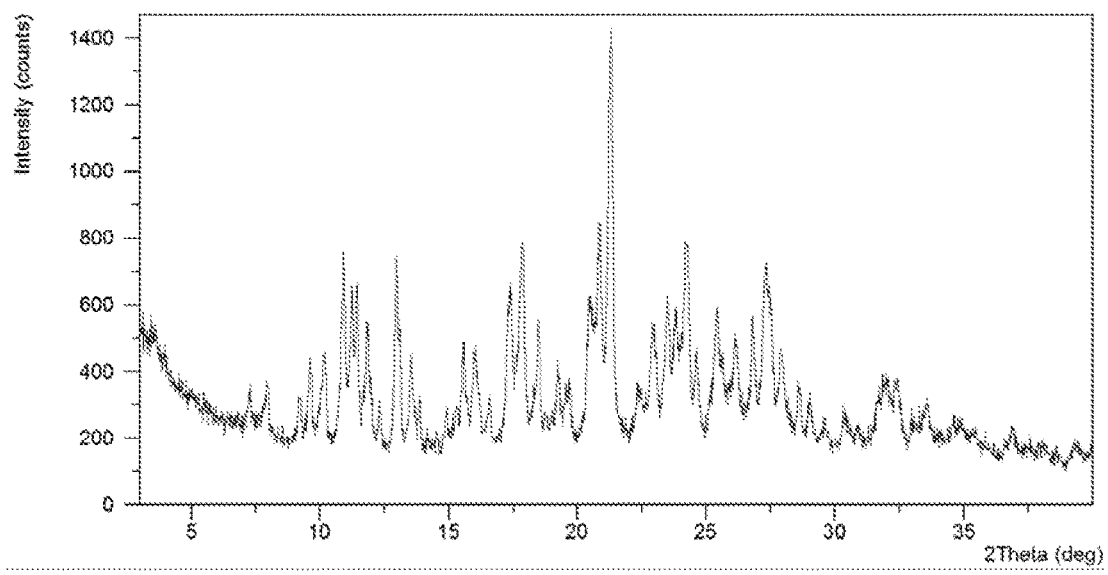
FIG. 26 shows an X-ray powder diffraction (XRPD) pattern of co-crystal composing lesinurad and glycolic acid.
Figure 27:
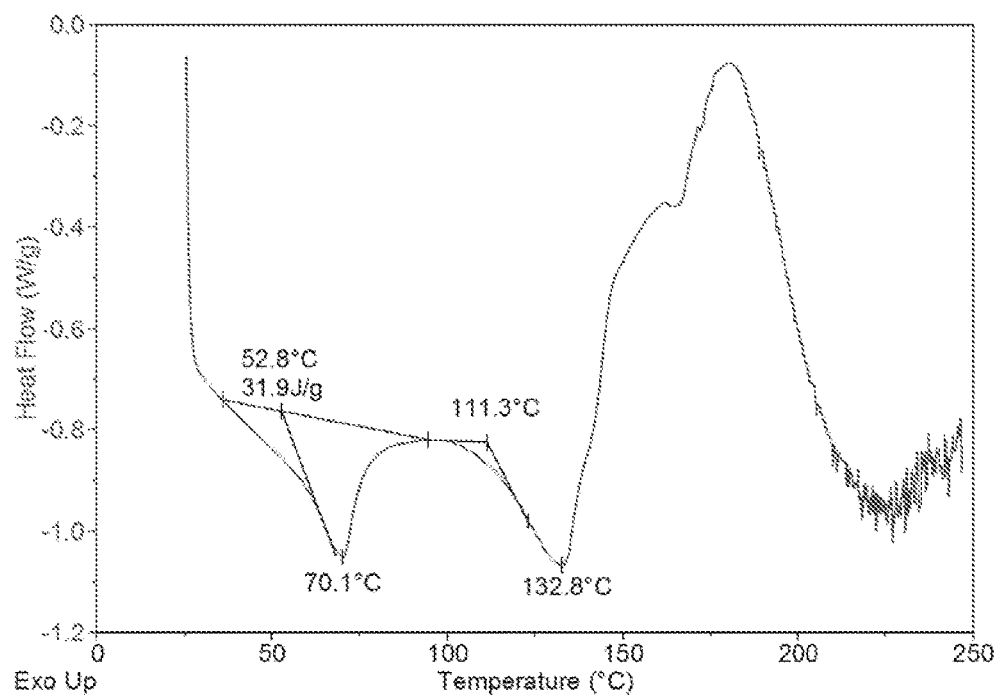
FIG. 27 shows a differential scanning calorimetric (DSC) thermogram of co-crystal composing lesinurad and glycolic acid.

To 0.3 mL of methanol was added 10 mg of lesinurad, followed by the addition of 1.9 mg of glycolic acid. The clear solution was evaporated to dryness under ambient conditions and co-crystal composing lesinurad and glycolic acid was obtained, which was analyzed by XRPD, DSC, and TGA. The XRPD pattern, DSC thermogram of co-crystal obtained from this example are displayed in FIGS. 26 and 27, respectively.

Co-crystal composing lesinurad and glycolic acid has a DSC thermogram comprising two endothermic peaks with onset temperature of about 52.8° C. and 111.3° C., and a TGA thermogram comprising about 10.0% weight loss up to 135.0° C.

What is claimed is:

1. A salt of the compound of formula (I):

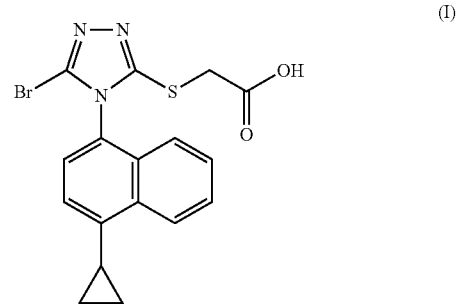 [SMILES: O=C(O)CSc1nnc(Br)n1-c1ccc(C2CC2)c2ccccc12]

which is a crystalline calcium salt Form A, having an X-ray powder diffraction pattern comprising peaks with 2-theta values: 8.5°, 4.2°, 17.1°, 19.9°, 20.5°, 21.4°, 23.8°, 25.1°, 25.8°, and 29.0°, said 2-theta values may vary by ±0.2°.

2. A process for preparing a salt according to claim 1, comprising dissolving lesinurad in two crystallization solvents; adding calcium hydroxide to form a mixture; and stirring the mixture to precipitate out the salt, wherein said two crystallizing solvents are a mixture of tetrahydrofuran and water.

3. The process of claim 2, wherein the mixture is stirred at ambient temperature or cooled to precipitate the salt.

4. A pharmaceutical composition comprising a salt according to claim 1 and a pharmaceutically acceptable carrier.

5. A method of treating or delaying the progression or onset of a disease or disorder in connection with activity of a URAT1 protein, comprising administering to a subject in need thereof a therapeutically effective amount of a salt according to claim 1, wherein said disease or disorder is selected from the group consisting of gout, a recurrent gout attack, gouty arthritis and hyperuricaemia.

* * * * *